(12) United States Patent
Sonderegger (10) Patent No.: US 8,412,300 B2
(45) Date of Patent: Apr. 2, 2013

(54) ARTERIAL FLASHBACK CONFIRMATION CHAMBER

(75) Inventor: Ralph L. Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 948 days.

(21) Appl. No.: 12/370,228

(22) Filed: Feb. 12, 2009

(65) Prior Publication Data

US 2010/0204553 A1 Aug. 12, 2010

(51) Int. Cl.
*A61M 5/32* (2006.01)
*A61B 5/055* (2006.01)

(52) U.S. Cl. .............. 600/345; 604/168.01; 604/167.03; 604/507

(58) Field of Classification Search ......................... None
See application file for complete search history.

(56) References Cited

U.S. PATENT DOCUMENTS

| | | |
|---|---|---|
| 2,868,200 A | 11/1954 | Gewecke |
| 4,187,860 A | 2/1980 | Villari |
| 4,365,630 A | 12/1982 | McFarlane |
| 4,710,173 A | 12/1987 | McFarlane |
| 4,714,461 A | 12/1987 | Gabel |
| 4,767,408 A | 8/1988 | McFarlane |
| 5,108,375 A | 4/1992 | Harrison et al. |
| 5,120,319 A | 6/1992 | Van Heugten et al. |
| 5,242,414 A | 9/1993 | Fischell et al. |
| 5,267,971 A | 12/1993 | Brimhall |
| 5,295,969 A | 3/1994 | Fischell et al. |
| 5,295,970 A | 3/1994 | Clinton et al. |
| 5,501,671 A | 3/1996 | Rosen et al. |
| 5,810,780 A | 9/1998 | Brimhall et al. |
| 5,984,895 A | 11/1999 | Padilla |
| 6,042,566 A | 3/2000 | Bhitiyakul |
| 6,261,263 B1 | 7/2001 | Huet et al. |
| 6,277,100 B1 | 8/2001 | Raulerson et al. |
| 6,979,323 B2 | 12/2005 | Rogers et al. |
| 7,261,703 B2 | 8/2007 | Lampropoulos et al. |
| 2005/0015071 A1 | 1/2005 | Brimhall |
| 2005/0245868 A1* | 11/2005 | Brown .......................... 604/122 |

\* cited by examiner

*Primary Examiner* — Shanon A Foley
(74) *Attorney, Agent, or Firm* — Jeanne Lukasavage; Craig Metcalf; Kirton McConkie (57) ABSTRACT

The present invention relates to an arterial flashback confirmation chamber. Generally, the confirmation chamber is used with a vascular access device to allow an operator to see active arterial flashback confirmation for a period of time that is long enough to permit the operator to properly place the cannula of the vascular access device within a patient's artery. In some instances, the confirmation chamber comprises a flashback compartment, means for prolonging active arterial flashback confirmation, and a vent. Some examples of suitable prolonging means comprise a flashback compartment with a relatively large internal volume, circuitous tubing, an absorbent material, an orifice and/or tubing with a smaller inner diameter than the inner diameter of the cannula, and the like. Where the vascular access device comprises a catheter assembly, the catheter assembly and confirmation camber are optionally used with a guide wire and/or a blood sensor.

12 Claims, 6 Drawing Sheets

ARTERIAL FLASHBACK CONFIRMATION CHAMBER

BACKGROUND OF THE INVENTION

The present invention relates to vascular access devices. More specifically, the present invention relates to an arterial flashback confirmation chamber that is configured to be attached to a vascular access device and to allow an operator to see arterial blood flashback confirmation for a prolonged period of time after the operator punctures an artery with a cannula from the access device.

Generally, vascular access devices are used for communicating fluid with the vascular system of patients. In one example, catheters are used for infusing fluid (e.g., saline solution, medicaments, and/or total parenteral nutrition) into a vein and/or withdrawing fluids (e.g., blood) from a vein. In another example, a catheter is inserted into a patient's artery (e.g., radial, brachial, femoral, pedal, carotid artery, etc.) to monitor blood pressure in real-time, to obtain samples for arterial blood gas measurements, to withdraw blood, and/or to deliver fluids (e.g., chemotherapeutic agents) directly into the patient's arterial blood supply.

Intravenous (IV) catheter assemblies are among the various types of vascular access devices that may be used to access both veins and arteries. Over-the-needle peripheral IV catheters are a common IV catheter configuration. As its name implies, an over-the-needle catheter is mounted over an introducer needle having a sharp distal tip. The introducer needle is generally a hypodermic needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel.

Currently, in order to verify proper placement of the needle and/or the catheter in a patient's blood vessel, an operator often confirms that there is a flashback of blood within the catheter assembly. Generally, this flashback comprises a small amount of blood, which flows from within the needle's lumen, through a notch disposed near the needle's distal tip, and into a space between the needle's outer surface and the inner surface of the transparent catheter. As blood continues to flow proximally through the catheter and into an extension tube, the operator sees the active flow of blood and is able to confirm that the needle's distal tip is still within the patient's blood vessel. If, however, the operator observes that blood has stopped flowing into the catheter and/or the extension tube, the operator may determine that the needle's tip has been pushed completely through the blood vessel or that the vessel has been transfixed. In response to this observation, the operator may reposition the needle until blood begins to flow into the catheter and extension tube, confirming proper needle and catheter placement.

Although many conventional catheter assemblies that are capable of providing flashback visualization may help an operator determine proper needle and/or catheter placement, such assemblies may also have shortcomings. In one example, some conventional catheter assemblies may place the operator at risk of being exposed to high-pressure arterial blood.

In another example, while some catheter assemblies allow blood to flow from a low-pressure vein into the catheter and extension tube for a relatively long period of time, the same assemblies may only allow blood to flow from an artery, with a higher pressure than the vein, for a relatively short time period before the blood completely fills the catheter and extension tube. Accordingly, when an operator attempts to place a catheter in an artery, the operator may observe that as the cannula punctures the artery, blood quickly rushes into and fills the catheter and extension tube. As a result, the operator may not be able to observe additional blood flowing into the assembly for a period of time that is sufficient to allow the operator to carefully and properly place the needle within the artery. For instance, once arterial blood fills the catheter and extension tube, the operator may not visually confirm a reduction of blood flow into the catheter and extension tube when the operator pushes the needle tip completely through the artery. As a result, the operator of certain conventional catheter assemblies may have difficulty determining proper needle and catheter placement within arteries.

Accordingly, there is a need in the art for a flashback confirmation assembly that provides active arterial flashback confirmation for a prolonged period of time without exposing the operator or others to high-pressure arterial blood. Such a flashback confirmation assembly is disclosed herein.

BRIEF SUMMARY OF THE INVENTION

The present invention relates to an arterial flashback confirmation chamber, or a confirmation chamber, that is designed to overcome the limitations mentioned above. Indeed, in some instances, the described arterial flashback confirmation chamber is configured to allow an operator to see active arterial flashback confirmation for a longer period of time than would be possible with a conventional catheter assembly in which the operator simply observes flashback within the catheter and extension tube. Accordingly, the described flashback confirmation chamber can allow the operator to watch blood actively flow into the flashback compartment for a period of time that is sufficient to allow the operator to carefully and properly place the needle and catheter tip within a patient's artery.

The described flashback confirmation chamber may comprise any component or characteristic that allows it to provide active arterial flashback confirmation for a period that is sufficient to allow the operator to properly place the cannula and/or catheter tip of a catheter assembly within the patient's artery. Some examples of suitable components comprise a flashback compartment, means for prolonging active arterial flashback confirmation, and a vent.

Generally, the flashback compartment comprises a cavity that is adapted to receive blood from a patient's blood vessel (e.g., artery) and allow the operator to watch the compartment progressively fill with blood when the cannula and/or catheter of the catheter assembly is properly disposed within the patient's blood vessel. The flashback compartment may comprise any suitable characteristic. In one example, at least a portion of the flashback compartment is transparent to allow the operator to watch the compartment fill with blood. In another example, the compartment can be any suitable shape, including being substantially cylindrical, cuboidal, spiral, spherical, irregular, tubular, etc.

The means for prolonging active arterial flashback confirmation may comprise any component or characteristic that allows an operator to see active arterial flashback confirmation in the flashback compartment for a period of time that is long enough to allow the operator to properly and carefully place the needle within a patient's artery. Some examples of suitable prolonging means comprise a flashback compartment with a relatively large internal volume, circuitous tubing, an absorbent material, an orifice or tubing with an inner diameter that is smaller than an inner diameter of the cannula of the vascular access device, and/or another component or characteristic that is capable of prolonging the amount of time during which an operator can see active arterial flashback confirmation.

Where the prolonging means comprises a flashback compartment with a relatively large internal volume, the prolonging means may increase the time in which the operator can observe the active arterial flashback by allowing more blood to enter the compartment than is possible in certain conventional catheter assemblies that lack the described confirmation chamber. Accordingly, the flashback compartment may have any suitable internal volume that allows it to fulfill its intended purpose. In one example, the compartment has an internal volume between about 1 cubic centimeters ("cc") and about 500 cc. In another example, the volume of the compartment is from about 3 cc to about 100 cc. In still another example, the internal volume of the compartment is from about 5 cc to about 15 cc.

Where the prolonging means comprises circuitous tubing, the circuitous tubing may have any suitable characteristic. For example, the circuitous tubing can be packed within the flashback compartment. In this example, the circuitous tubing may be packed in any suitable manner, including by being coiled, zigzagged, or randomly packed in the flashback compartment. In another example, the circuitous tubing may be any suitable length, including between about 2.5 centimeters ("cm") and about 200 cm, between about 10 cm and about 50 cm, and between about 15 cm and about 25 cm.

Where the prolonging means comprises an absorbent material, the absorbent material may have any suitable characteristic that allows the confirmation chamber to fulfill its intended purposes. In one example, the absorbent material is packed within the flashback compartment in a manner that allows the material to become visibly and progressively saturated with blood. In such embodiments, the absorbent material may comprise any suitable medical-grade blood-absorbing material, such as cotton, polyester, polyethylene fibers, etc.

Where the prolonging means comprises tubing and/or an orifice having a smaller inner diameter than the inner diameter of the cannula of the vascular access device, the tubing and/or orifice may have any characteristic that allows the tubing and/or the orifice to limit the rate at which blood flows into the flashback compartment. For example, the inner diameter of the tubing and/or the orifice may be any amount smaller than the cannula's inner diameter that allows the confirmation chamber to function as intended. For instance, the inner diameter of the tubing and/or the orifice may be between about 5% and about 99%, between about 25% and about 80%, or between about 50% and about 75% of the inner diameter of the cannula.

As previously mentioned, the arterial flashback confirmation chamber also comprises a vent. While the vent can perform any suitable function, in some instances, the vent allows air to exit the flashback compartment as blood enters the catheter, the extension tube, and/or the flashback compartment. The vent may comprise any component or characteristic that allows it to fulfill its intended purposes. In one example, the vent comprises a material that is permeable to air and impermeable to blood. Some examples of such materials include polyethylene terephthalate, a microfiber matter, a synthetic material comprising high-density polyethylene fiber (e.g., TYVEK® material from DuPont), GORE-TEX®, and the like.

In addition to the aforementioned components, the arterial flashback confirmation chamber may comprise any other suitable component. In one example, the confirmation chamber comprises a valve that both allows blood to enter the flashback compartment and retains the blood within the compartment. In another example, the confirmation chamber comprises a surface or mechanism for connecting the confirmation chamber to a vascular access device as an add-on component.

The confirmation chamber may be used with any suitable device, system, and/or technique. By way of example, while the confirmation chamber is described as being used with a catheter assembly, the confirmation chamber may be used with any suitable vascular access device, including a phlebotomy kit.

Where the confirmation chamber is used with a catheter assembly, the catheter assembly may be used with any other suitable component that allows the confirmation chamber to fulfill its intended purpose. In one example, the catheter assembly is used with a guide wire to assist the cannula in fully entering the artery. In another example, the cannula assembly comprises an attached sensor, such as an electronic pressure transducer, that can be used to measure characteristics of the patient's arterial blood.

While the following discussion focuses on using the arterial flashback confirmation chamber for observing flashback from a patient's artery, the described device can be used to observe flashback from any portion of a patient's vasculature. For example, the described confirmation chamber may be used with a vascular access device to observe flashback confirmation from a patient's vein.

BRIEF DESCRIPTION OF THE SEVERAL VIEWS OF THE DRAWINGS

In order that the above-recited and other features and advantages of the invention are obtained and will be readily understood, a more particular description of the invention briefly described above will be rendered by reference to specific embodiments thereof, which are illustrated in the appended drawings. These drawings depict only typical embodiments of the invention and are not therefore to be considered to limit the scope of the invention.

DETAILED DESCRIPTION OF THE INVENTION

The presently preferred embodiments of the described invention will be best understood by reference to the Figures, wherein like reference numbers indicate identical or functionally similar elements. It will be readily understood that the components of the present invention, as generally described and illustrated in the Figures, could be arranged and designed in a wide variety of different configurations. Thus, the following more detailed description, as represented in FIGS. 1 through 8, is not intended to limit the scope of the invention as claimed, but is merely representative of some presently preferred embodiments of the invention.

This disclosure describes an arterial flashback confirmation chamber that can be added to a vascular access device to prolong the period of time in which an operator may observe active arterial flashback confirmation from the assembly. As used herein, the term active arterial flashback confirmation may refer to the act of blood continuously flowing from a patient's artery (e.g., radial, brachial, femoral, pedal, carotid artery, etc.) into a receptacle that allows the operator to observe the receptacle fill, at least partially, with blood. By increasing the amount of time that the operator can observe active arterial flashback confirmation, the described arterial flashback confirmation chamber can increase the amount of time that an operator has to properly and carefully place the catheter while being able to visually confirm proper catheter placement.

Figure 1:
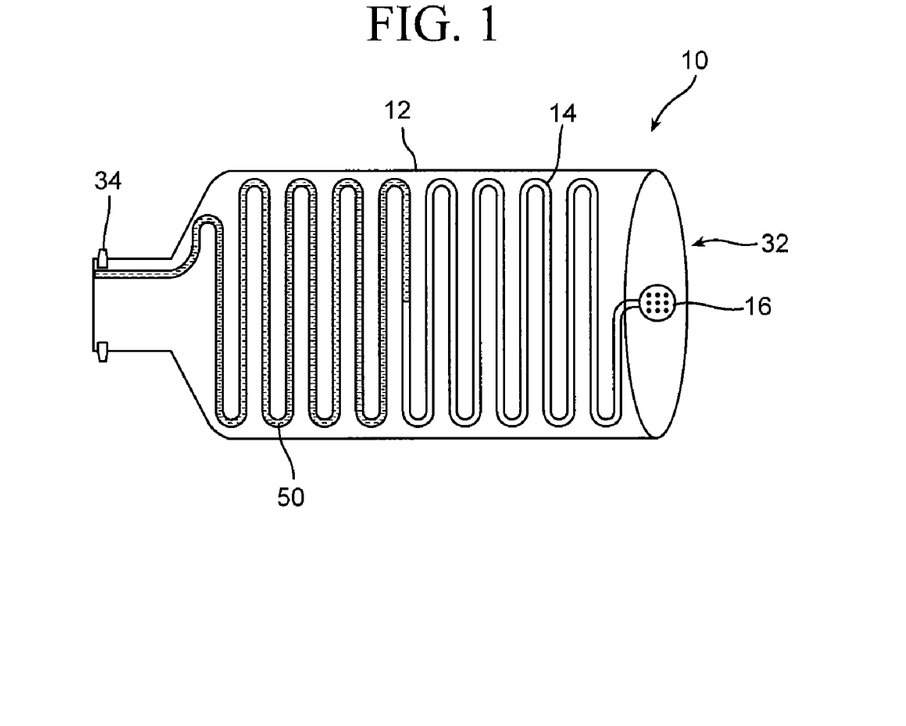
FIGS. 1-2 each illustrate a side plan view of a representative embodiment of an arterial flashback confirmation chamber comprising circuitous tubing.

The arterial flashback confirmation chamber may comprise any component that allows (1) the operator to visualize blood filling the confirmation chamber once the cannula of the vascular access device punctures the patient's vasculature, (2) allows the operator to visualize a decrease (i.e., a cessation) of blood flow into the chamber if the distal tip of the cannula is pushed completely through the patient's blood vessel or the blood vessel is transfixed, and (3) allows the chamber to prolong the period of time in which the operator can observe active arterial flashback confirmation from the vascular access device. By way of illustration, FIG. 1 depicts a representative embodiment in which the arterial flashback confirmation chamber 10 comprises a flashback compartment 12, means for prolonging active arterial flashback confirmation (e.g., tubing 14), and a vent 16. To provide a better understanding of the flashback confirmation chamber, each of the aforementioned components is described below in more detail.

In some embodiments, the arterial flashback confirmation chamber comprises a flashback compartment. While this compartment may serve many purposes, in some embodiments, the flashback compartment is configured to receive blood from the patient's vasculature and to allow the operator to visualize the blood. The flashback compartment may comprise any characteristic or component that allows it to fulfill these stated functions. Indeed, in some embodiments, at least a portion of the flashback compartment comprises a translucent or a transparent material that allows the operator to watch the chamber progressively fill with blood. While any suitable portion of the flashback compartment may be translucent/transparent, FIG. 1 illustrates an embodiment in which most, if not all, of the flashback compartment 12 is fabricated of a transparent material.

The flashback compartment may be any shape that allows it to fulfill its intended purposes. For instance, the flashback compartment may be substantially cylindrical, cuboidal, elongated cuboidal, elliptical, spherical, conical, spiral, irregular, tubular, polygonyl, conical, and/or any other suitable shape. By way of illustration, FIG. 1 shows a representative embodiment in which the flashback compartment 12 is substantially cylindrical.

Additionally, the flashback compartment may fill with blood in any suitable manner. For example, blood can flow in a proximal, distal, axial, lateral, or any other suitable direction. In some presently preferred embodiments, however, FIG. 1 shows that as blood 50 progressively fills the flashback compartment 12, the blood 50 flows proximally through the compartment.

As mentioned above, in some embodiments, the flashback compartment further comprises means for prolonging active arterial flashback confirmation. The prolonging means may comprise any suitable component with any suitable characteristic that allows the confirmation chamber to provide a vascular access device with active arterial flashback confirmation for a period of time that is longer than the vascular access device could provide without the confirmation chamber. Some examples of suitable prolonging means comprise circuitous tubing, a flashback compartment with a relatively large internal volume, an absorbent material, an orifice and/or tubing which a smaller inner diameter than the inner diameter of the vascular access device's cannula, and/or any other component that is capable of restricting the rate of blood flow into the flashback compartment, and/or capable of increasing the time during which the chamber fills with blood.

In some embodiments, the prolonging means comprises a section of circuitous tubing. While such a section of circuitous tubing may fulfill any suitable purpose, in some embodiments, the circuitous tubing allows blood to flow through a relatively long tube that is compacted into a small, easy-to-handle package. Where the prolonging means comprises circuitous tubing, the tubing may have any suitable characteristic. In one example, the tubing is placed within the flashback compartment. In this example, the tubing can be placed within the flashback compartment in any suitable manner, including by being zigzagged, coiled, randomly packed, or the like. By way of illustration, FIGS. 1 and 2 respectively illustrate representative embodiments in which the confirmation chamber 10 comprises tubing 14 that is zigzagged and coiled within flashback compartment 12.

In another example, the circuitous tubing may be any suitable length. For instance, in some embodiments, the tubing is between about 2.5 cm and about 200 cm in length. In other embodiments, the tubing is between about 10 cm and about 50 cm. In still other embodiments, the tubing is between about 15 cm and about 25 cm in length.

In some embodiments, the prolonging means comprises a flashback compartment having an internal volume that is relatively large, as compared to the internal volume of the catheter and/or extension tube of the vascular access device. In such embodiments, the flashback compartment may allow more blood to flow through the cannula of the vascular access device than would be possible if the vascular access device did not comprise the described confirmation chamber. To allow the flashback compartment to act as the prolonging means, the flashback chamber may comprise any suitable internal volume. In some instances, the flashback compartment 12 has an internal volume, as illustrated by 18 in FIG. 3, of between about 1 cc and about 500 cc. In other instances, the flashback chamber has an internal volume of between about 3 cc and about 100 cc. In yet other instances, the flashback chamber has an internal volume of between about 5 cc and about 15 cc.

Figure 4:
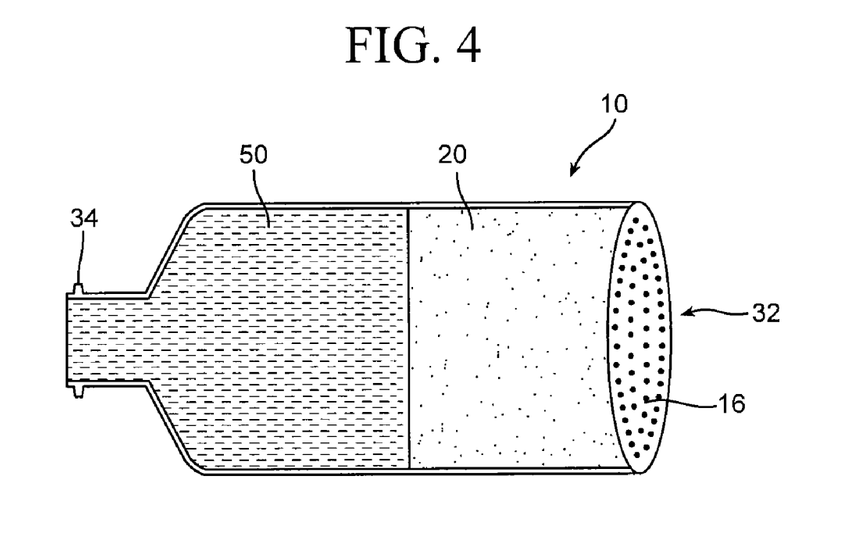
FIG. 4 illustrates a side plan view of a representative embodiment of the arterial flashback confirmation chamber, wherein the confirmation chamber comprises an absorbent material.

In other embodiments, the prolonging means comprises an absorbent material. For example, FIG. 4 illustrates a representative embodiment of the confirmation chamber 10 in which the flashback compartment 12 comprises an absorbent material 20. Where the prolonging means comprises an absorbent material, the absorbent material may comprise any suitable substance that is capable of visibly and progressively becoming saturated with blood as blood flows into the flashback compartment. For instance, the absorbent material may comprise any suitable medical-grade, blood-absorbing material, such as cotton, polyester, polyethylene fibers, cellulose material (e.g., gauze), fabric, and the like.

Figure 5A:
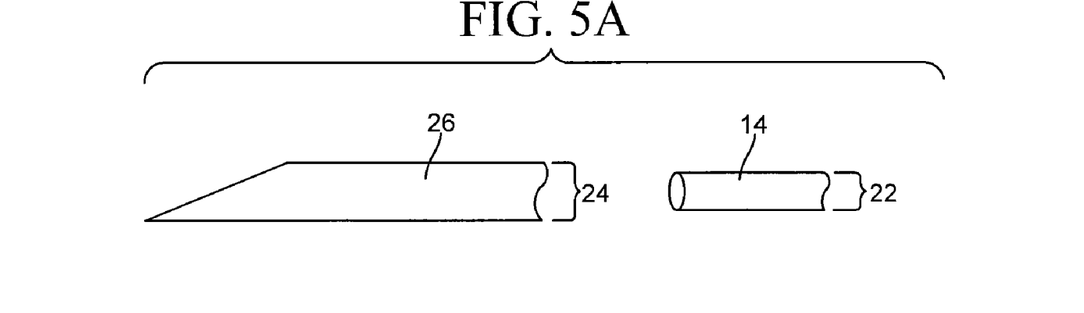
FIG. 5A illustrates a side plan view of a representative embodiment of a cannula and tubing, wherein the tubing has an inner diameter that is smaller than an inner diameter of the cannula.
Figure 5B:
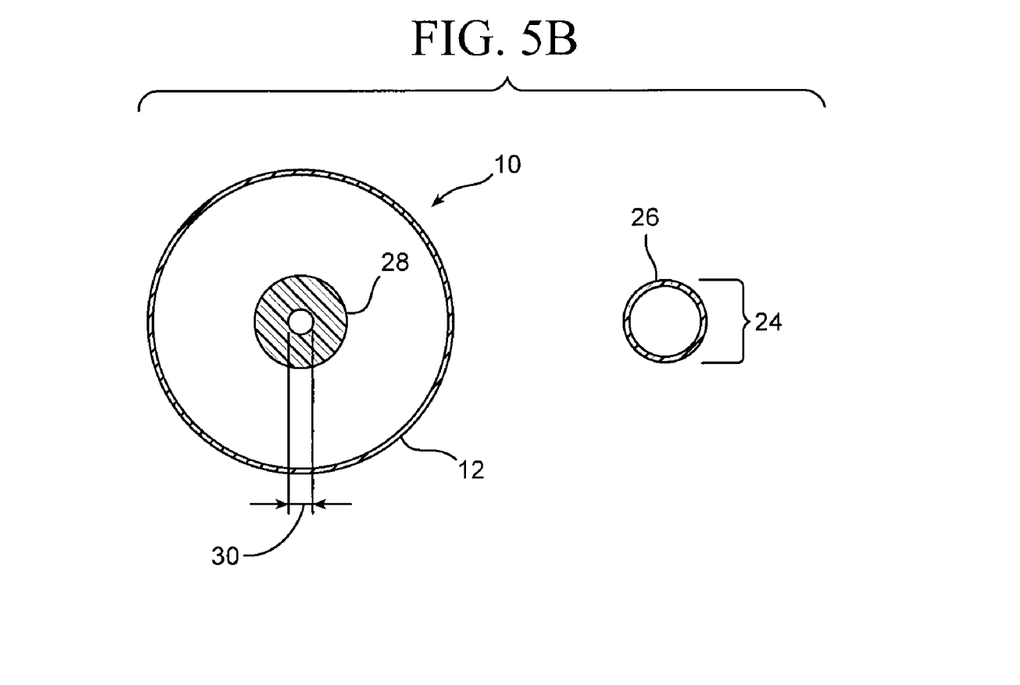
FIG. 5B illustrates a face plan view of a representative embodiment of the arterial flashback confirmation chamber and the cannula, wherein the confirmation chamber comprises an orifice with a smaller inner diameter than the inner diameter of the cannula.

In still other embodiments, the prolonging means comprises an orifice and/or tubing in the confirmation chamber that has an inner diameter that is smaller than the inner diameter of the vascular access device's cannula. By forcing blood from the patient's artery through the smaller diameter of the tubing and/or orifice, the blood's flow is slowed and the time of active arterial flashback confirmation can be extended. Additionally, because the tubing and/or the orifice within the confirmation chamber has a reduced inner diameter and not the catheter, a vascular access device comprising the confirmation chamber having an orifice or tubing with a reduced inner diameter may prolong flashback confirmation without affecting the amount of fluids that can pass through the catheter once then confirmation chamber is removed, closed, or otherwise prevented from filling with additional blood.

Where the prolonging means comprises an orifice and/or tubing within the confirmation chamber that has a smaller inner diameter than the inner diameter of the vascular access device's cannula, the orifice and/or tubing (e.g., tubing 14) may have any characteristic that allows the orifice and/or tubing to limit the rate at which blood flows into the flashback compartment. In one example, the inner diameter of the orifice/tubing is between about 5% and about 99% as long as the cannula's inner diameter. In another example, the inner diameter of the orifice/tubing is between about 25% and about 80% as long as the cannula's inner diameter. In still another example, the inner diameter of the orifice/tubing is between about 50% and about 70% the length of the cannula's inner diameter. For instance, FIG. 5A illustrates a representative embodiment in which the tubing 14 from the flashback compartment (not shown comprises an inner diameter 22 that is about 25% as long as the inner diameter 24 of the cannula 26. Similarly, FIG. 5B illustrates a representative embodiment in which an orifice 28 that opens into the flashback compartment 12 has an inner diameter 30 that is about 33% as long as the inner diameter 24 of the cannula 26.

The prolonging means (e.g., circuitous tubing, etc.) may be modified for any suitable purpose and in any suitable manner. For instance, the prolonging means may be modified in any suitable manner to adjust for differing blood pressures. In one example, where the prolonging means comprises circuitous tubing, the circuitous tubing may be longer for embodiments that are to be used with patients having relatively high arterial blood pressure (e.g., adults) and shorter for patient's having relatively low arterial blood pressure (e.g., children). In a second example, where the prolonging means comprises a relatively large internal volume in the flashback compartment, a flashback compartment for use with a patient having a relatively high arterial pressure may be larger than the flashback compartment that is configured for use with a patient having a relatively low arterial blood pressure. In a third example, where the prolonging means comprises an absorbent material, the absorbent material may be packed more densely for a confirmation chamber that is to be used for a patient with a relatively high blood pressure than it would be for a patient having a relatively low blood pressure. In a final example, where the prolonging means comprises an orifice/tubing that has a smaller inner diameter than the inner diameter of the cannula, the inner diameter of the orifice/tubing may be smaller for a confirmation chamber that is to be used for a patient having a relatively high pressure than it would be for a patient having a relatively low blood pressure.

As previously mentioned, the confirmation chamber also comprises a vent. The vent can perform any suitable function, including allowing air to exit the flashback compartment as blood enters the catheter, extension tube, and/or flashback compartment. The vent 16, which is depicted in FIGS. 1 through 4, may be disposed in any suitable location. By way of example, FIGS. 1 through 4 show the vent 16 can be disposed at the proximal end 32 of the confirmation chamber 10.

The vent may also comprise any component or characteristic that allows it to fulfill its intended purpose. In one example, the vent comprises a material that is permeable to air and impermeable to blood, including, but not limited to, polyethylene terephthalate ("PET"), a microfiber matter, a synthetic material comprising high-density polyethylene fiber (e.g., TYVEK® material from DuPont), GORE-TEX®, and the like. While the use of such materials may offer several benefits, in some embodiments, such air-permeable, blood-impermeable materials prevent blood from exiting the flashback compartment through the vent and exposing the operator and others to potential blood exposure.

In some embodiments, the vent is also configured to be adjustable so that the operator can change the rate at which air flows through the vent when the confirmation chamber is being used. In other words, in some embodiments, the vent is adjustable in a manner that allows the operator to change the rate at which blood flows into the flashback compartment. Accordingly, in some embodiments, the vent can also be used as the prolonging means. In such embodiments, the vent can be adjusted in any suitable manner. By way of example, the vent can comprise an adjustable aperture or a conventional valve (e.g., a stopcock valve) that can be adjusted (e.g., partially and/or completely opened or closed) by the operator to optimize the blood flow rate for a particular patient's arterial blood pressure.

Figure 2:
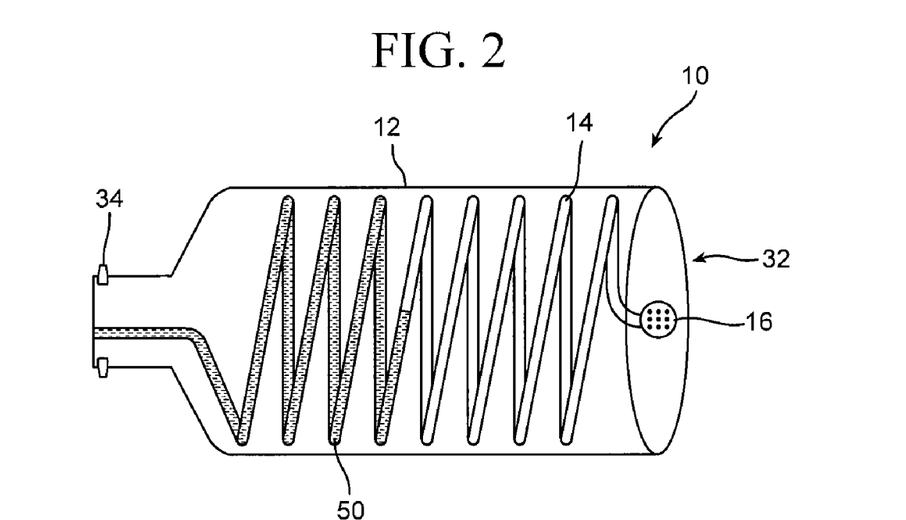
Figure 3:
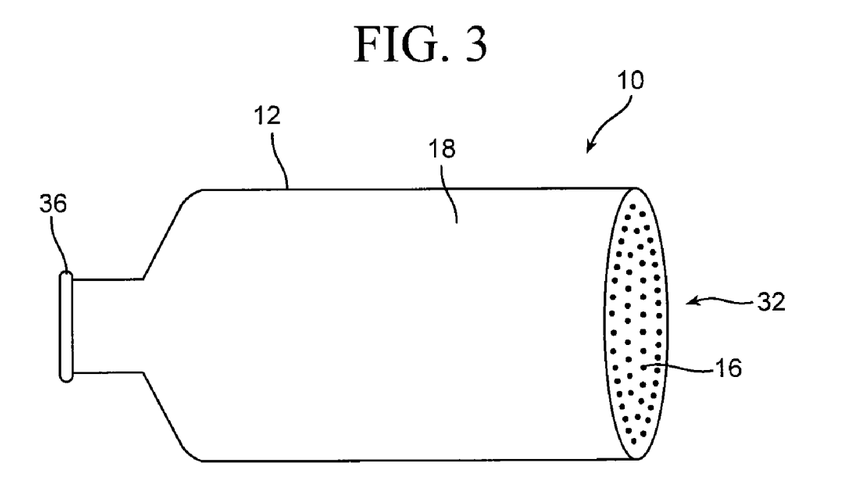
FIG. 3 illustrates a side plan view of a representative embodiment of the arterial flashback confirmation chamber, wherein the confirmation chamber comprises a flashback compartment comprising a relatively larger internal volume.

In addition to the previously mentioned components and characteristics, the arterial flashback confirmation chamber may be modified in any suitable manner. For example, the confirmation chamber may be connected to a vascular access device in any suitable manner. For instance, the confirmation chamber may be integrally connected to the vascular access device or be adapted to be selectively coupled and uncoupled from the vascular access device as an add-on device.

Where the confirmation chamber is adapted to be selectively coupled to and uncoupled from the vascular access device, the confirmation chamber comprise any component that allows the confirmation chamber to be selectively coupled to and uncoupled from the vascular access device. For instance, the confirmation chamber can comprise a connection adapter, or a surface/component that is configured to mechanically connect to a component of the vascular access device. By way of example, FIGS. 1, 2, and 4 show embodiments in which the connection adapter comprises a threaded engagement 34 (e.g., a LUER LOCK®). Similarly, FIG. 3 shows an embodiment in which the connection adapter comprises a lip 36 that is configured to be clamped or otherwise mechanically connected to a component of the vascular access device (discussed below).

In another example of a suitable modification, the confirmation chamber may comprise a blood valve, or a valve that allows blood to enter the flashback compartment without escaping back through the valve. Such a valve may serve several purposes. For instance, the blood valve may allow blood to be trapped within the flashback compartment so that the confirmation chamber can be safely disposed of (e.g., in a biohazard sharps collector) without allowing the operator or others to be exposed to blood that entered the flashback compartment.

The blood valve may comprise any valve that is capable of trapping blood in the flashback compartment once the blood has entered the compartment through the valve. Some examples of suitable valves comprise a conventional one-way valve (e.g., a ball check valve, a diaphragm check valve, a clapper valve, a stop check, a lift check valve, etc.), a stopcock valve, a septum, or any other valve that is configured to trap blood within the flashback chamber while allowing the confirmation chamber to fulfill its intended purposes.

Figure 6:
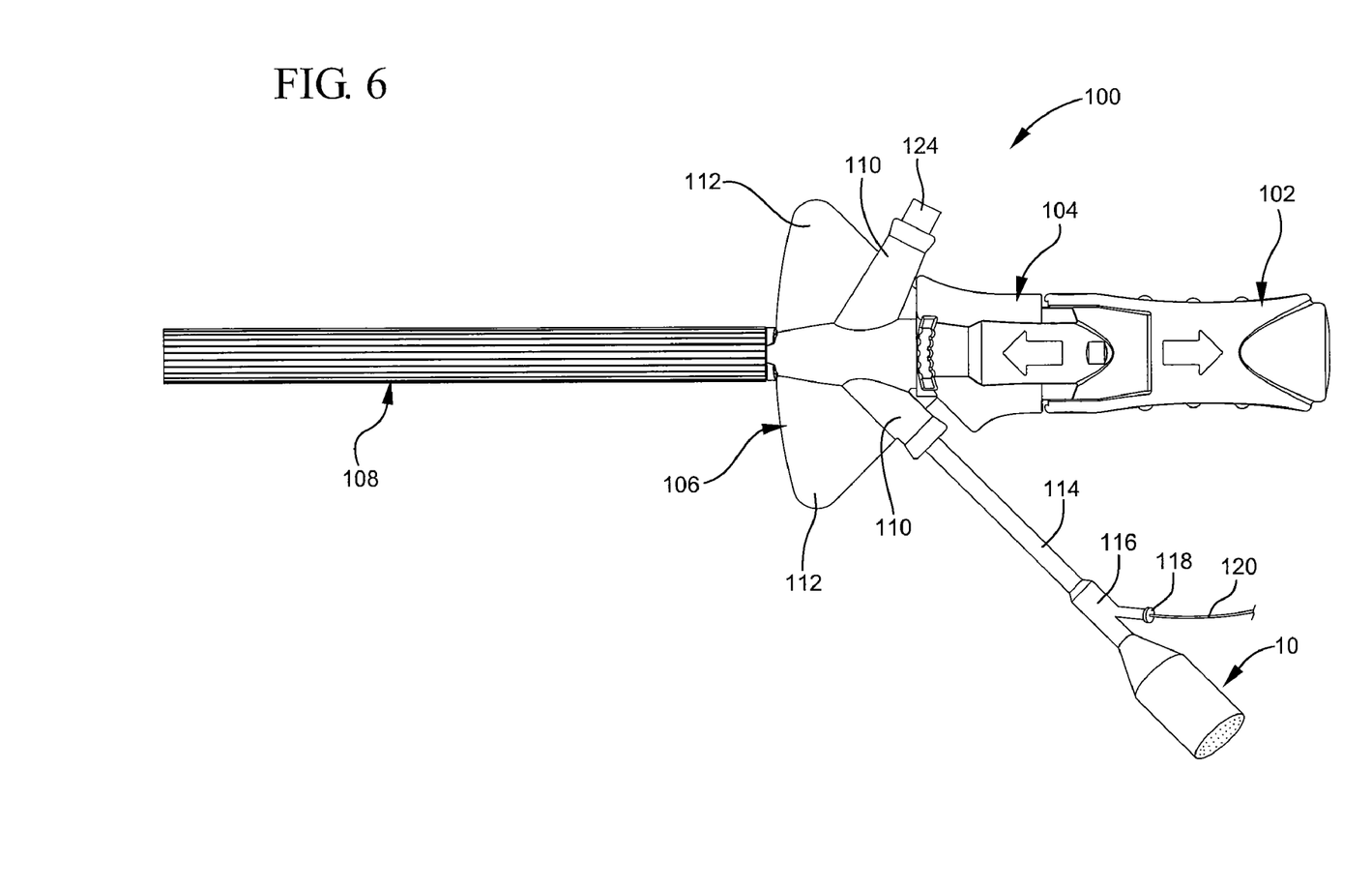
FIG. 6 illustrates a top plan view of a representative IV catheter assembly.

The confirmation chamber may be used with any suitable vascular access device. As used herein, the term vascular access device may refer to virtually any device that is configured to puncture and to introduce or withdraw material (e.g., a fluid) from the patient's vasculature. Some examples of suitable vascular access devices comprise an intravenous ("IV") catheter assembly (i.e., a peripheral and a central IV), a phlebotomy kit, an infusion kit, an introducer kit, a hypodermic needle and syringe, and the like. However, to provide a better understanding of the confirmation chamber, the following description focuses on using the chamber with an IV catheter assembly.

Where the confirmation chamber is used with an IV catheter assembly, the catheter assembly may comprise practically any IV catheter assembly that can be used with the described confirmation chamber. Some examples of such catheter assemblies comprise an over-the-needle catheter assembly, a peripheral IV catheter assembly, a central IV catheter assembly, a closed IV catheter assembly, and combinations thereof. By way of example, FIG. 6 illustrates a representative embodiment in which the confirmation chamber 10 is used with an over-the-needle, closed IV catheter assembly 100. As used herein, the term closed catheter assembly may refer to a catheter assembly comprising one or more seals, septa, and/or other components that contain blood within the catheter assembly during use and prevent blood from leaking from the catheter assembly after use.

A closed IV catheter assembly may comprise any suitable component. For instance, FIG. 6 shows an embodiment in which the catheter assembly 100 comprises a needle hub 102, a needle shield 104, a catheter adapter 106, and a needle sheath 108, which covers a needle and catheter (not shown in FIG. 6). As illustrated, each of the components (e.g., 102, 104, 106, and 108) of the catheter assembly 100 is configured to cooperate as an integrated apparatus. As more clearly illustrated in FIG. 7, each of the components 102, 104, 106, and 108 of the catheter assembly 100 comprise individual units with features adapted to provide specific functionality to the catheter assembly 100.

The various components of the catheter assembly may comprise any suitable component. For example, FIG. 7 shows the catheter adapter 106 may include one or more access ports 110, catheters 111, catheter wings 112, or any other feature determined to be beneficial to the operation of the catheter assembly 100.

Where the catheter assembly comprises an access port, the access port may serve any suitable purpose. In one example, FIG. 7 shows a representative embodiment in which an access port 110 allows the confirmation chamber 10 to be in fluid communication with the catheter adapter 106. While the confirmation chamber 10 may be connected to the access port 110 in any suitable manner, FIG. 7 shows an embodiment in which the confirmation chamber 10 is connected to the access port 110 via an extension tube 114 and a Y-adapter 116.

Figure 7:
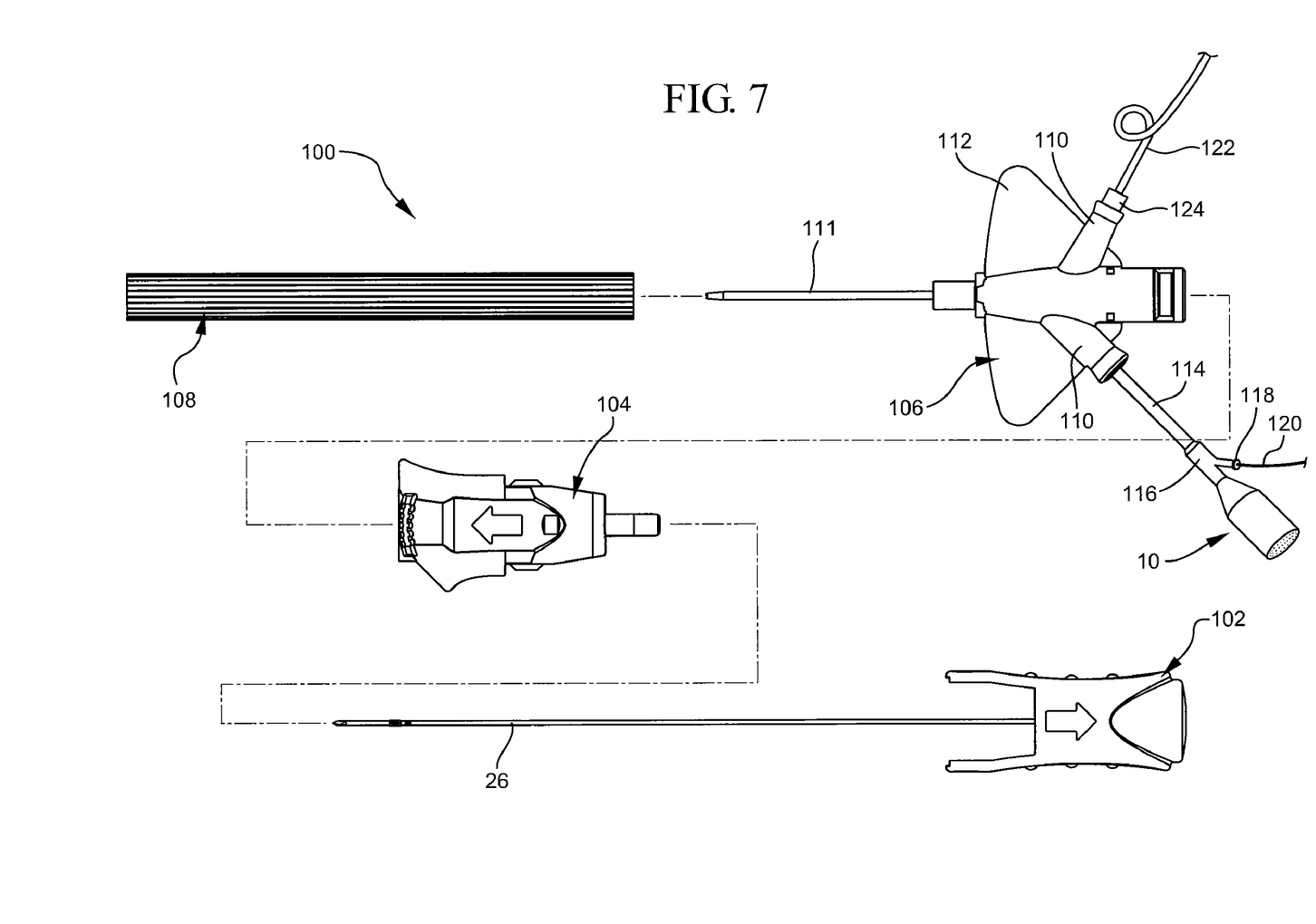
FIG. 7 illustrates an exploded, top plan view of the IV catheter assembly of FIG. 6.

In another example of a suitable use for the access port, FIG. 7 shows that the access port 110 can be used to connect an electronic sensor 118 to the catheter assembly 100. In this example, the electronic sensor may comprise any suitable sensor, including a pressure transducer, a temperature transducer, and/or another sensor that is capable of measuring characteristics of the patient's blood. Additionally, FIG. 7 shows that the electronic sensor 118 can comprise wiring 120 to electrically connect the sensor 118 to an appropriate device (not shown).

In still another example, FIG. 7 shows that an access port 110 can be used to allow a guide wire 122 to be inserted into the catheter adapter 106. While the guide wire 122 can be inserted into the access port 110 in any suitable manner, FIG. 7 shows that, in at least some embodiments, the guide wire 122 is inserted through a conventional septum 124, which prevents fluids (e.g., blood) from exiting the access port 110.

Such a guide wire can be used in any suitable manner. For example, once the cannula tip has punctured the patient's artery and been pushed completely through the artery so that the operator notices a decrease of blood into the flashback chamber, the cannula tip may be pulled back into the artery until the operator notices an increase in the rate at which blood flows into the chamber. Once the operator has ensured the cannula tip is within the artery, the wire guide can be inserted through the cannula so as to extend distally in the patient's vasculature, past the cannula's distal tip. At that point, the cannula can be pushed further into the artery, following the guide wire, until the cannula is fully inserted into the artery. Once the cannula is properly placed, the guide wire can be extracted from the catheter assembly.

In a final example of a use for the access port, the access port 22 can be modified to include an infusion source, such as a section of intravenous tubing and an intravenous fluid pouch (not shown). For instance, once the confirmation chamber has been used to ensure proper catheter placement, the chamber can be removed from the catheter assembly and the infusion source may be connected catheter assembly (e.g., via the extension tube 114 and/or Y-adapter 116).

Figure 8:
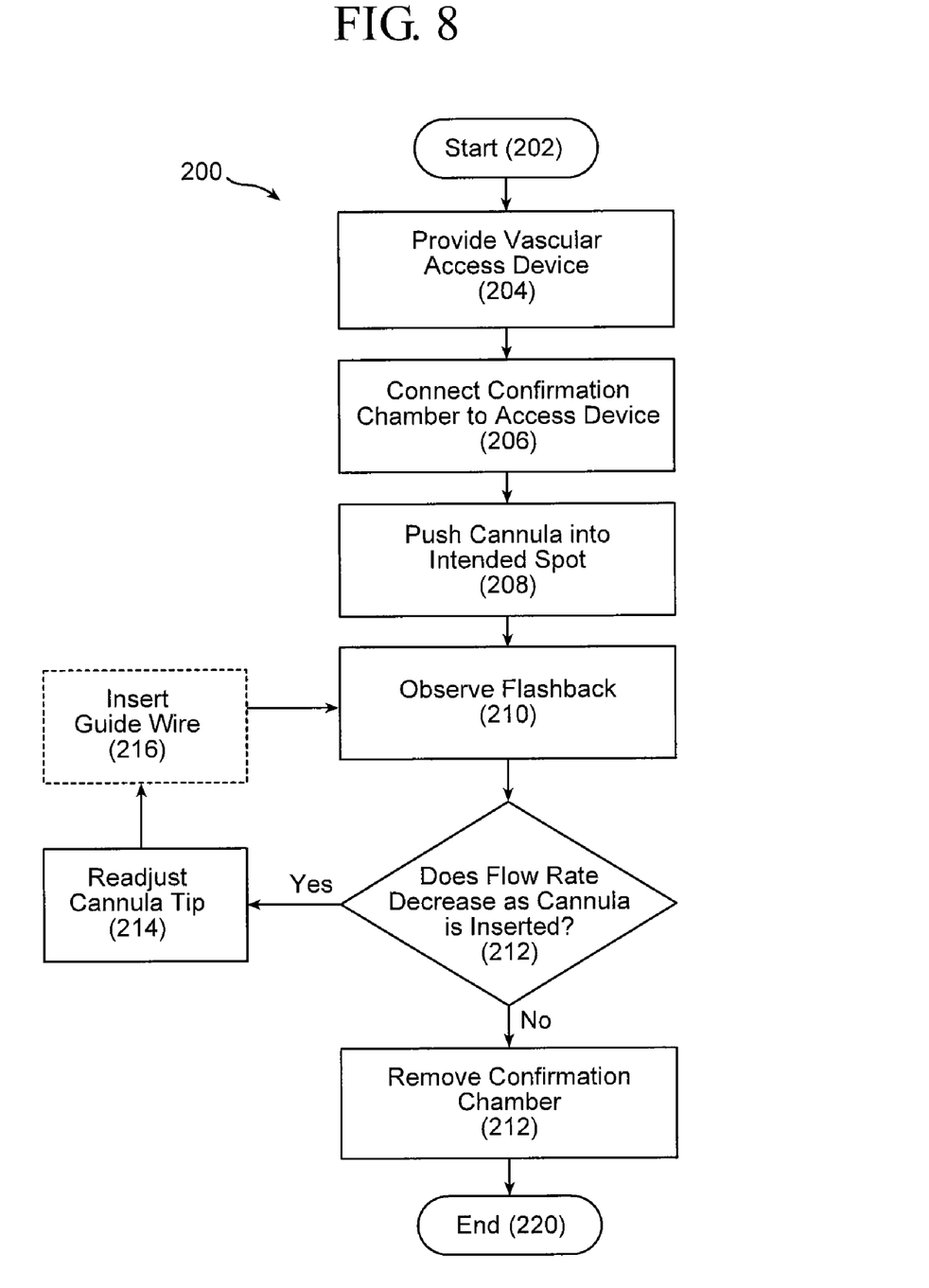
FIG. 8 illustrates a flowchart of a representative embodiment of a method for using the arterial flashback confirmation chamber.

The described confirmation chamber can be used in any suitable manner. By way of example, FIG. 8 illustrates a flowchart depicting a representative embodiment of a method for using the confirmation chamber. Specifically, after starting at 202, box 204 shows the method 200 continues by providing a vascular access device, such as a catheter assembly. Box 206 shows the method 200 continues as the operator connects the confirmation chamber to the access device.

Next, box 208 shows the operator punctures the patient's skin with the cannula of the access device and pushes the cannula tip into the patient's artery (e.g., the radial artery). Once the operator punctures the artery, the operator is able to blood flowing into the flashback compartment. Then, as the operator moves the cannula tip to ensure proper placement, box 212 shows the operator determines whether the amount of blood flowing into the flashback confirmation compartment is decreased. If the operator observes that the rate at which blood flows into the flashback compartment does decrease, box 214 shows the operator may readjust the cannula tip and box 216 shows the operator may optionally insert a guide wire into the catheter assembly. After readjusting the cannula tip, FIG. 8 shows the method 200 returns to box 210, where the operator observes the flashback.

Once the operator observes that blood is flowing into the flashback compartment at a suitable rate, box shows the confirmation chamber can be removed so the catheter assembly can be used as intended. Finally, FIG. 8 shows the method ends at 220, where the blood-containing confirmation chamber is discarded.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An arterial flashback confirmation chamber comprising:
    A transparent flashback compartment having a a proximal end and a distal end;
    a vent that is permeable to air and impermeable to blood, the vent comprising a portion of the proximal end of the transparent flashback compartment;
    a connector comprising a portion of the distal end of the transparent flashback compartment; and
    a section of tubing having a distal opening and a proximal opening, the proximal opening being positioned at the proximal end of the transparent flashback compartment, and the distal opening being positioned at the distal end of the transparent flashback compartment, the tubing being deposited within the transparent flashback compartment and spanning a distance between the proximal end and the distal end of the transparent flashback compartment, the section of tubing having an overall length that is greater than an overall length of the transparent flashback compartment.

2. The confirmation chamber of claim 1, wherein the section of tubing comprises an internal volume of the transparent flashback compartment that is between about 1 cubic centimeter and about 500 cubic centimeters.

3. The confirmation chamber of claim 2, wherein the internal volume of the transparent flashback compartment is between about 5 cubic centimeters and about 15 cubic centimeters.

4. The confirmation chamber of claim 1, wherein the section of tubing comprises circuitous tubing.

5. The confirmation chamber of claim 1, wherein the section of tubing comprises an inner diameter that is smaller than an inner diameter of a cannula of a vascular access device to which the flashback confirmation chamber is connected.

6. The confirmation chamber of claim 1, wherein the vent is adjustable to change the rate at which blood flows into the transparent flashback compartment.

7. The confirmation chamber of claim 1, wherein the connector is configured to connect the flashback confirmation chamber to a vascular access device as an add-on device.

8. A closed arterial IV catheter system comprising;
    a closed arterial IV catheter adapter having a catheter access port; and
    a transparent arterial flashback confirmation chamber having a proximal end and a distal end, the distal end having a connector configured to attach to the catheter access port, wherein the transparent arterial flashback confirmation chamber comprises:
    a vent that is permeable to air and impermeable to blood, the vent comprising a portion of the proximal end of the transparent arterial flashback confirmation chamber; and
    a section of tubing having a distal opening and a proximal opening, the proximal opening being positioned at the proximal end of the transparent arterial flashback confirmation chamber, and the distal opening being positioned at the distal end of the transparent arterial flashback confirmation chamber, the tubing being deposited within the transparent arterial flashback confirmation chamber and spanning a distance between the proximal end and the distal end of the transparent arterial flashback confirmation chamber, the section of tubing having an overall length that is greater than an overall length of the transparent arterial flashback confirmation chamber; and
    a valve that allows blood to enter the flashback compartment and then retains the blood within the compartment.

9. The system of claim 8, wherein the section of tubing comprises circuitous tubing.

10. The system of claim 8, wherein the section of tubing comprises an internal volume of the transparent arterial flashback confirmation chamber that is between about 1 cubic centimeter and about 500 cubic centimeters.

11. The system of claim 10, wherein the internal volume of the transparent arterial flashback confirmation chamber is between about 5 cubic centimeters and about 15 cubic centimeters.

12. The system of claim 10, wherein the section of tubing comprises an inner diameter that is smaller than an inner diameter of a cannula of a vascular access device to which the transparent arterial flashback confirmation chamber is connected.

* * * * *